(12) United States Patent
Deguchi et al.

(10) Patent No.: US 7,790,457 B2
(45) Date of Patent: Sep. 7, 2010

(54) SOLID CELLULOSIC CULTURE MEDIUM AND PROCESS FOR PRODUCING THE SAME

(75) Inventors: Shigeru Deguchi, Yokosuka (JP); Mikiko Tsudome, Yokosuka (JP); Susumu Ito, Yokosuka (JP); Koki Horikoshi, Yokosuka (JP)

(73) Assignee: Japan Agency for Marine-Earth Science and Technology, Yokosuka-shi (JP)

( * ) Notice: Subject to any disclaimer, the term of this patent is extended or adjusted under 35 U.S.C. 154(b) by 857 days.

(21) Appl. No.: 10/591,288

(22) PCT Filed: Feb. 28, 2005

(86) PCT No.: PCT/JP2005/003813

§ 371 (c)(1),
(2), (4) Date: Feb. 22, 2007

(87) PCT Pub. No.: WO2005/083056

PCT Pub. Date: Sep. 9, 2005

(65) Prior Publication Data

US 2007/0172938 A1   Jul. 26, 2007

(30) Foreign Application Priority Data

Mar. 2, 2004   (JP)   ............... 2004-057618

(51) Int. Cl.
   *C12N 5/00*   (2006.01)
   *A61K 9/00*   (2006.01)
(52) U.S. Cl. ...................... 435/404; 424/488
(58) Field of Classification Search ............... 435/404; 424/488
   See application file for complete search history.

(56) References Cited

U.S. PATENT DOCUMENTS 6,258,586 B1 *   7/2001   Jussila et al. ............... 435/252

FOREIGN PATENT DOCUMENTS

| JP | 55-44312 | 3/1980 |
|---|---|---|
| JP | 63-32252 | 12/1988 |
| JP | 7-48470 | 2/1995 |
| JP | 9-19285 | 1/1997 |
| JP | 10-195103 | 7/1998 |
| JP | 2002-153264 | 5/2002 |
| JP | 2004-049129 | 2/2004 |

OTHER PUBLICATIONS

Mikiko Tsuru, et al., "Kessho Cellulose Gels o Mochiita shinki Biseibutsu Baiyoho", Japan Society for Bioscience, Biotechnology, Mar. 5, 2004, p. 40 (2A10p25).
Shigeru Deguchi, et al., "Takoshitsu Cellulose o Mochiita Shinki Biseibutsu Baiyoho", The Chemical Society of Japan Koen Yoko, vol. 84, Mar. 11, 2004, p. 1171 (3J6-53).
Mikiko Tsuru, et al., "Takoshitsu Cellulose o Mochiita Shinki Biseibutsu Baiyoho", Journal of Japanese Society for Extremophiles, vol. 3, No. 2, Nov. 25, 2004, pp. 104-105.
Shigenori Kuga, et al., "The Porous Structure of Cellulose Gel Regenerated from Calcium Thiocyanate Solution", Journal of Colloid and Interface Science, vol. 77, No. 2, Oct. 1980, pp. 413-417.
Daniel Shungu, et al., "Gelrite as an Agar Substitute in Bacteriological Media", Applied and Environmental Microbiology, vol. 46, No. 4, Oct. 1983, pp. 840-845.
New Experimental Biochemistry Lecture Series No. 17, Mar. 23, 1992, 3 Cover Pages and pp. 15-20.

* cited by examiner

*Primary Examiner*—Ruth A Davis
(74) *Attorney, Agent, or Firm*—Oblon, Spivak, McClelland, Maier & Neustadt, L.L.P.

(57) ABSTRACT

The present invention relates to a solid medium containing as a medium-solidifying component a cellulose gel, in particular a cellulose gel which is a porous cellulose gel structure containing cellulose as the skeletal part and having a cellulose concentration of 0.01% or higher and a porosity of 50% or higher, as well as a process for producing the same. The solid medium of the invention can be obtained by dispersing cellulose in a solvent, especially an aqueous thiocyanate salt solution, stirring and/or heating the dispersion to dissolve the cellulose, subsequently cooling the solution and/or removing the solvent to cause the solution to gel, and permeating nutrients into the resultant cellulose gel.

The solid medium usable under a wide range of culture conditions where conventional solid media such as agar medium cannot be used, as well as a method for producing the same is provided.

8 Claims, 1 Drawing Sheet

SOLID CELLULOSIC CULTURE MEDIUM AND PROCESS FOR PRODUCING THE SAME

TECHNICAL FIELD

The present invention relates to a solid medium for use in culturing microorganisms and the like as well as a method for producing the same. More specifically, the invention relates to a solid medium using as a medium-solidifying component a cellulose gel, as well as a method for producing the same.

BACKGROUND ART

Methods for culturing microorganisms include methods with liquid media and methods with solid media. The methods using liquid media are problematic in that bacterial growth is weak; no mutant strains can be obtained; or only bacteria at low purity can be isolated. Because methods using solid media have fewer such problems by which distinctly separated colonies can be formed, alternatively, the methods are excellent as methods for isolating microorganisms and culturing the microorganisms at high purity. Thus, the methods have been used traditionally. As a solidifying component for the solid media, agar gel has been used traditionally since the era of Dr. Koch. As described in for example "New Experimental Biochemistry Lecture Series No. 17" (edited by the Japan Biochemistry Association, 1992, issued by Tokyo Kagaku Dojin), page 15 to page 20, agar gel is a hard and transparent solid in a wide temperature range where bacteria can grow, so the number of microorganisms decomposing agar is very limited. Thus, agar gel has such excellent properties that the problematic liquefaction scarcely occurs. Accordingly, agar gel is very great as a medium-solidifying agent. It is no exaggeration to say that no excellent medium-solidifying agent replacing the agar gel has been found yet.

However, such agar gel is softened or dissolved, depending on the condition such as temperature pH or salt concentration. Thus, the range where agar gel can be used as a medium-solidifying component is limited to a given condition. So as to screen for new useful microorganisms, recently, it is required to culture microorganisms in a wider range of culture conditions including for example temperature, pH and salt concentration. Therefore, it is desired to develop a medium-solidifying component usable in such a wider range of culture conditions. For example, ultra-thermophilic bacteria capable of growing at a temperature as high as 121° C. have been identified so far. Enzymes generated by such ultra-thermophilic bacteria are believed to be industrially useful. However such bacteria cannot be cultured in solid media because the temperature for the growth of such microorganisms is the softening temperature of agar or higher. Therefore, such bacteria have been prepared only by liquid culturing. As described above, however, the growth thereof by liquid culturing is weak; no mutant strains can be obtained; or the purity of the isolated bacteria is low. Compared with the solid culturing thereof, the liquid culturing thereof is significantly limited.

Various attempts have been made to develop a medium-solidifying component usable in a wider range of culture conditions. For example, a method using as a medium-solidifying component gellan gum (see for example Shungu, D., Valiant, M., Tutlane, V., Weniberg, E., Weissberger, B., Koupal, L., Gadebusch, H., and Stapley, E., "Appl. Environ. Microbial.", 1983, 46, 840-845), as well as a culture process on a silica gel plate containing a medium (see for example New Experimental Biochemistry Series No. 17, page 15 to page 20, edited by the Japan Biochemistry Association, 1992, issued by Tokyo Kagaku Dojin) has been developed. The method using gellan gum is however disadvantageous in that a medium cannot be solidified when cations (metal cations, in the medium are insufficient or in that the increase of the acidity causes poorer solidification of a medium. The method using such silica gel plate is disadvantageous in that the use thereof is tough under alkaline conditions; the resulting plate has a lower water retention capacity and the surface of the plate is readily dried, leading to the occurrence of adverse influences on microbial growth. In other words, it should be said that no solid medium satisfactorily applicable under culture conditions including a wide range of temperature pH and salt concentration has been developed yet.

It is an object of the invention to overcome the problems of related-art solid media such as agar medium sometimes never usable depending on the condition such as temperature, pH or salt concentration as described above and provide a solid medium usable in a wider range of culture conditions and a method for producing the same.

DISCLOSURE OF THE INVENTION

The present inventors made investigations so as to solve the problems of the related-art solid media as described above The inventors found that these problems could be solved by using a cellulose gel as a medium-solidifying medium. Thus, the invention has been achieved.

Specifically the invention can be summarized in the following contents.

(1) A solid medium containing a cellulose gel as a medium-solidifying component.

(2) A solid medium described above in (1), where the crystallization degree of the cellulose gel is 5 to 70%.

(3) A solid medium described above in (1) or (2), where the molecular weight of the cellulose used is 10,000 to 2,000,000.

(4) A solid medium described above in any of (1) through (3), where the cellulose gel is a porous cellulose gel structure with a cellulose backbone and at a cellulose concentration of 0.01% or more.

(5) A solid medium described above in any of (1) through (4), where the cellulose gel is a porous gel-like structure at a porosity of 50% or more.

(6) A solid medium described above in any of (1) through (5), where the cellulose gel is a porous gel-like material obtained by heating and dissolving cellulose in an aqueous thiocyanate salt solution and subsequently cooling the resulting solution.

(7) A method for producing a solid cellulose gel medium, including dissolving or swelling cellulose dispersed in a solvent by mechanical mixing and/or heating, subsequently solidifying the resulting cellulose by cooling and/or solvent removal and permeating nutrient components into the resulting cellulose.

(8) A method for producing a solid cellulose gel medium as described above in (7), including dissolving cellulose dispersed in a solvent by heating, subsequently cooling and solidifying the resulting solution from which the solvent component is removed, and permeating nutrient components into the resulting cellulose.

(9) A method for producing a solid cellulose gel medium as described above in (7) or (8), where the solvent is an aqueous solution of an alkali metal salt or alkali earth metal salt of thiocyanic acid.

(10) A method for producing a solid cellulose gel medium as described above in any of (7) through (9), where the solvent is an aqueous solution of calcium thiocyanate.

(11) A method for producing a solid cellulose gel medium as described above in any of (7) through (10), where the solvent is an aqueous saturated solution of calcium thiocyanate and the heating temperature is 70 to 200° C.
(12) A method for culturing a microorganism or a cell, including culturing a microorganism or a cell on the surface of a solid medium using a cellulose gel as a medium-solidifying component.
(13) A method for culturing a microorganism as described above in (12), where the microorganism cultured on the solid medium using a cellulose gel is a microorganism in extreme environment.

The solid medium using a cellulose gel as a medium-solidifying component in accordance with the invention has various properties and shapes stable at a higher temperature, in a wide pH range or in a wide range of salt concentration. Therefore the solid medium with great properties can be produced. Without any occurrence of softening or dissolution in a wide range of culture conditions the solid medium can be used. Thus, the solid medium can establish the culturing of microorganisms and the like, under severe conditions such as a high temperature of more than 100° C., or pH of 3 or less or pH of 10 or more, which has never been made on a solid medium using agar as a typical related-art solid medium.

BEST MODE FOR CARRYING OUT THE INVENTION

Figure 1:
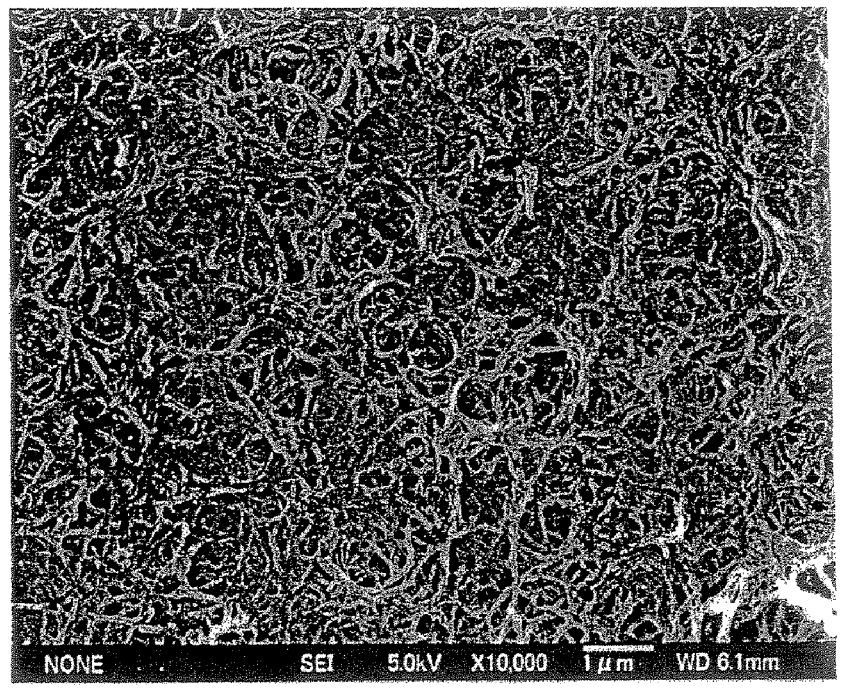
FIG. 1 is a scanning electron microscope picture showing the surface state of the cellulose gel used in the solid medium of the invention, at magnification×10,000.

The cellulose for producing the cellulose gel used in accordance with the invention is polysaccharides of glucose generated in a plant or a microorganism and linearly bonded together via β-1,4-glucoside bond, or various derivatives thereof. The cellulose derivative for producing the cellulose gel in accordance with the invention includes for example branched or esterified derivatives thereof, such as nitrate ester, phosphate ester, xanthogenate salt, nitrite ester, nitrate ester, sulfate ester, formate ester, acetate ester, propionate ester, butyrate ester, valerate ester, acetate propionate ester, acetate butyrate ester, trifluoroacetate ester, benzoate ester, tosyl ester, phenyl carbanilate, alkylketene dimer ester, and alkenyl succinic anhydride ester; etherified derivatives thereof such as carboxymethyl cellulose, methyl cellulose, ethyl cellulose, propyl cellulose, hydroxyethyl cellulose, methylhydroxyethyl cellulose, hydroxypropyl cellulose, methylhydroxypropyl cellulose, ethylhydroxyethyl cellulose, cyanoethyl cellulose, diethylaminoethyl ethyl cellulose, trimethylammonoylhydroxypropyl cellulose, and triphenylmethyl cellulose; halogenated derivatives thereof as prepared by introduction of fluorine, chlorine, bromine and iodine; or cellulose derivatives such as amino group-introduced derivatives thereof, thiol group-introduced derivatives thereof, polymer-grafted derivatives thereof, and oxide derivatives of polyuronate type thereof. Such derivatives may be derivatives chemically modified after the cellulose gel is obtained. These cellulose or derivatives thereof preferably have a molecular weight of 10,000 to 2,000,000. Particularly, the cellulose or derivatives thereof are α-cellulose of a molecular weight of 10,000 to 100,000.

The cellulose gel for use in accordance with the invention can be obtained by dissolving or swelling such cellulose or a derivative thereof as described above in a solvent and subsequently recrystallizing or solidifying the resulting cellulose or a derivative thereof.

The dissolution of celluloses in a solvent is influenced by the size of cellulose molecule, the actions of hydroxyl group or oxygen atom in the pyranose ring in the cellulose molecule and the like in a complicated manner. The cellulose gel for use in accordance with the invention can be obtained by dispersing and mixing celluloses in a solvent, dissolving or swelling the celluloses under heating if necessary, and subsequently solidifying the celluloses by cooling if necessary, from which the solvent is removed.

As the solvent for dissolving cellulose or a derivative thereof, there can be used or example aqueous solutions of inorganic acids such a hydrochloric acid, sulfuric acid, nitric acid and phosphoric acid; solutions of alkalis such as lithium hydroxide and sodium hydroxide; aqueous solutions of inorganic compounds such as zinc chloride, thiocyanate salts, liquid ammonia/thiocyanate salts, liquid ammonia/sodium liquid ammonia/ammonium iodide, and hydrazine; solutions of metal complexes such as $[Cu(NH_3)_4](OH)$, $[Cu(ethylenediamine)_2](OH)_2$, $[Co(ethylenediamine)_2](OH)_2$, $[Ni(NH_3)_2](OH)_2$, $[Ni(ethylenediamine)_3](OH)_2$, $[(Cd(ethylenediamine)_3](OH)_2$, $[Zn(ethylenediamine)_3](OH)_2$, Fe:tartaric acid:NaOH; a mixture of one or two or more selected from organic solvents such as dimethylsulfoxide/formaldehyde, N,N-dimethylformamide/formaldehyde, N,N-dimethylacetamide/formaldehyde, dimethylsulfoxide/chloral, N,N-dimethylformamide/chloral, N,N-dimethylacetamide/chloral, dimethylsulfoxide/chloral/pyridine, N,N-dimethylformamide/chloral/pyridine, N,N-dimethylacetamide/chloral/pyridine, dimethylsulfoxide/chloral/triethylamine, N,N-dimethylformamide/chloral/triethylamine, N,N-dimethylacetamide/chloral/triethylamine, dimethylsulfoxide/anhydrous sulfurous acid/diethylamine, N,N-dimethylformamide/anhydrous sulfurous acid/diethylamine, dimethylsulfoxide/anhydrous sulfurous acid/triethylamine, N,N-dimethylformamide/anhydrous sulfurous acid/triethylamine, dimethylsulfoxide/anhydrous sulfurous acid/piperidine, N,N-dimethylformamide/anhydrous sulfurous acid/piperidine, dimethylsulfoxide/anhydrous sulfurous acid/isoamylamine, N,N-dimethylformamide/anhydrous sulfurous acid/isoamylamine, dimethylsulfoxide/$N_2O_4$, N,N-dimethylformamide/$N_2O_4$, dimethylsulfoxide/NOCl, N,N-dimethylformamide/NOCl, dimethylsulfoxide/$NOSO_4H$, N,N-dimethylformamide/$NOSO_4H$, N,N-dimethylacetamide/lithium chloride, N-methyl-2-pyrrolidone/lithium chloride, 1,3-dimethyl-2-imidazolidinone/lithium chloride, N,N-dimethylacetamide/lithium bromide, N-methyl-2-pyrrolidone/lithium bromide, 1,3-dimethyl-2-imidazolidinone/lithium bromide, trifluoroacetic acid, trifluoroacetic acid/chloroform, trifluoroacetic acid, trifluoroacetic acid/acetic acid, N-methylmorpholine-N-oxide hydrous salt, N-methylmorpholine-N-oxide hydrous salt/dimethylsulfoxide, and N-alkylpyridinium halogens.

Among them, an aqueous thiocyanate salt solution is the most preferable as such solvent, because the solution when used swells cellulose to increase further the facial interval of cellulose crystal faces; the cellulose is dissolved by further heating, which is then cooled and solidified into a gel-like forms to form a porous gel-like structure suitable as the solid medium of the invention. Such thiocyanate salt preferably includes for example alkali metal salts of thiocyanic acid, such as sodium thiocyanate and potassium thiocyanate, and alkali earth metal salts of thiocyanic acid, such as calcium thiocyanate and magnesium thiocyanate. Particularly, an aqueous calcium thiocyanate solution containing calcium thiocyanate at a mass concentration of 40% or more or an aqueous sodium thiocyanate solution containing sodium thiocyanate at a mass concentration of 50% or more is preferable. An aqueous saturated calcium thiocyanate solution is the most preferable.

As the water to be used herein, additionally, purified water such as ultra-pure water, distilled water and deionized water is used. Tap water is also satisfactory.

The amount of cellulose to be added to a solvent for dissolving cellulose is with no specific limitation. The amount thereof is adjusted, depending on the molecular weight of cellulose, and the like. Generally, the amount is adjusted to 0.01 mass % or more, preferably about 0.01 to 20 mass % of the solvent, from the standpoint of ready procedure. The method for the dispersion into the solvent is with no specific limitation. Various such methods for general use may be used for the dispersion into the solvent. After cellulose is added to the solvent, alternatively, the resulting solvent is satisfactorily agitated in a simple manner. So as to obtain the cellulose gel of the invention, cellulose is dispersed and mixed in the solvent, which is further heated, if necessary, to swell cellulose and then dissolve the cellulose. Subsequently, the swollen or dissolved cellulose solution is cooled if necessary and solidified, from which the solvent is removed to form a porous cellulose gel suitable for use in accordance with the invention. To a solvent, then, the cellulose may be added at an amount above the solubility thereof in the solvent. In this case, the cellulose is cooled and solidified at a state of the cellulose partially not dissolved even after heating. Even the cellulose gel obtained in such manner is in a porous gel-like form, which is preferably used for the solid medium of the invention.

In case that a thiocyanate salt is used as the solvent, preferably, the cellulose is swollen and dissolved by heating in a solvent to preferably 70° C. or more, more preferably 80 to 200° C. Any heating means is used with no specific limitation. Generally, the cellulose is preferably heated using an autoclave or microwave, from the aspect of production efficiency. In case of using commercially available microcrystalline cellulose as the cellulose and an aqueous saturated calcium thiocyanate solution as the solvent, the cellulose can be dissolved by heating at 95° C. for about one minute.

From the cellulose gel in gellation, then, the cellulose is rinsed to remove the solvent component therein. In case that the solvent is a thiocyanate salt, any rinsing solvent capable of dissolving thiocyanate salt may be used as the rinsing solvent for use in rinsing the cellulose gel, which is for example water and a polar organic solvent. As such rinsing solvent, for example, a mixture of one or two or more selected from the group consisting of water, methanol, ethanol and acetone is preferably used. As the water to be used herein, purified water such as ultra-pure water, distilled water, and deionized water is used. Tap water may also be satisfactorily used. Any rinsing method may be used with no specific limitation. Rinsing may be done by immersion in running water, or by a method of immersion in a container and appropriate exchange of rinse water. From the aspect of rinsing efficiency, preferably, electrodialysis is used for rinsing. Additionally, the rinsing level of the cellulose gel can be determined by measuring the conductivity of the rinse solution.

Preferably, the crystallization degree of the obtained cellulose gel is 5 to 70%, particularly preferably 30 to 50%. The cellulose for use in the cellulose gel has a molecular weight of 10,000 to 2,000,000, preferably 10,000 to 100,000.

Figure 2:
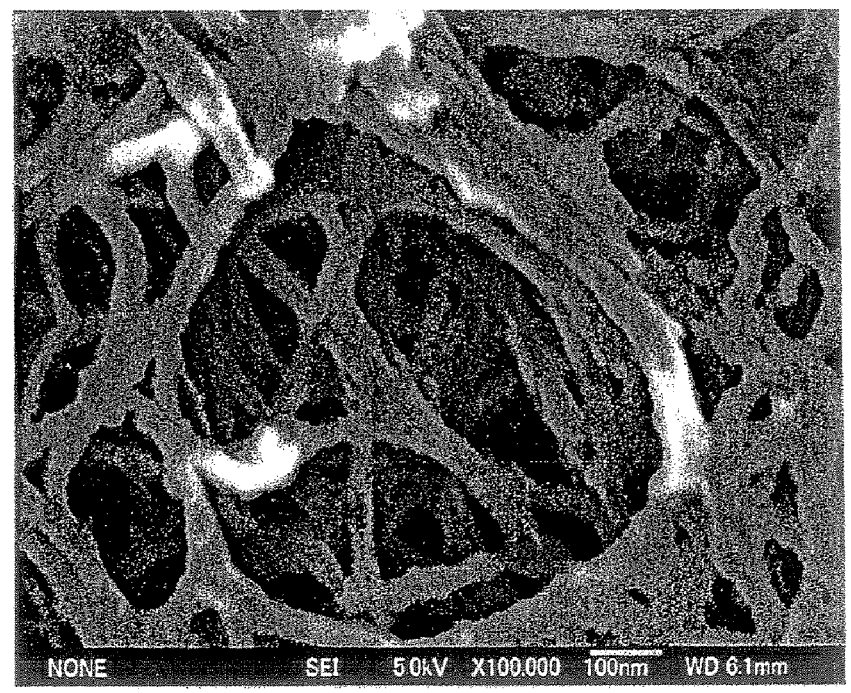
FIG. 2 is a scanning electron microscope picture showing the surface state of the cellulose gel used in the solid medium of the invention, at magnification×100,000.

The cellulose gel obtained in such manner is a porous cellulose gel structure with a cellulose backbone as shown in FIGS. 1 and 2, which contains very large pores at a cellulose concentration in the gel of 0.01% or more. The porosity of the porous cellulose gel structure is 50% or more. More preferably a porous cellulose gel structure of a porosity at 80 to 99.99% is used. When a medium containing various nutrient components is put in contact to such cellulose gel, the medium highly efficiently permeates into the inner pores of the solid cellulose gel, which incorporates the nutrient components, to form a solid medium.

In the solid cellulose gel medium of the invention, various media for use in the related-art agar medium may be used as they are. As naturally occurring media, for example, naturally occurring media containing as the main components naturally occurring substances such as meat juice, peptone, yeast extract, malt extract and serum may be used, along with commercially available synthetic media and the like. When these media are put in contact to the cellulose gel, solid cellulose gel media containing these nutrients may be prepared.

The solid cellulose gel medium in accordance with the invention may be in any shape with no specific limitation. The solid cellulose gel medium may be used as plate, slant, or high-layer media.

The thus obtained solid cellulose gel medium of the invention has properties stable at low temperature to fairly high temperature in a wide pH range. Even when the solid medium is heated to a high temperature, the medium is never softened or dissolved but retains the shape in a stable manner and has a great water retentivity so the medium is hardly dried. Thus, the solid cellulose gel medium can be used as a very great solid medium. Specifically the solid cellulose gel medium may be used in a temperature range of $-20°$ C. to $250°$ C. but is preferably used in a temperature range of $0°$ C. to $150°$ C. Additionally, the solid cellulose gel medium of the invention may be used in a stable manner in a wide range of pH 1 to pH 14 but is preferably used in a range of pH 2 to pH 12. Furthermore, the solid cellulose gel medium of the invention can be used as a medium, after the medium absorbs arbitrary concentration of salts while the medium retains the shape in a stable manner under no influence of the salt concentrations in a medium to be permeated.

The solid medium using the cellulose gel thus produced in accordance with the invention may be used under wider culture conditions concerning temperature and pH and can be used varieties of uses including culturing many types of microorganisms and cells.

Microorganisms suitable for culturing in the solid mediums using the cellulose gel of the invention include for example cellulase-generating bacteria, xylanase-generating bacteria, chitinase-generating bacteria, amylase-generating bacteria, mannanase-generating bacteria, mannosidase-generating bacteria, agarase-generating bacteria, pullulanase-generating bacteria, glucanase-generating bacteria, pectinase-generating bacteria, galactosidase-generating bacteria, alginase-generating bacteria, cyclodextrin synthase-generating bacteria, protease-generating bacteria, lipase-generating bacteria, catalase-generating bacteria, polyamine oxidase-generating bacteria, RNase-generating bacteria, DNase-generating bacteria, and DNA polymerase-generating bacteria.

Additionally microorganisms in extreme environment such as thermophilic bacteria, cryophilic bacteria, alkaliphilic bacteria, acidophilic bacteria, halophilic bacteria, barophilic bacteria and organic solvent-resistant bacteria can be cultured efficiently, by actively utilizing the characteristic properties of the solid medium using the cellulose gel of the invention. The solid medium can effectively be used for culturing microorganisms under conditions in extreme environment, such as ultra-thermsophilic bacteria growing at high temperature more than 80° C., acidophillc bacteria growing at high acidity such as pH 2 or lower, and alkaliphilic bacteria growing at high alkalinity such as pH 12 or more.

The invention is described in more detail in the following Examples. However, these Examples never limit the invention. Herein, the "%" in the Examples represents % on a mass basis unless otherwise stated.

In the Examples below, the individual media used in culturing microorganisms were prepared as follows.

(A) LB Medium (pH 7):
10 g of trypton, 5 g of yeast extract, and 10 g of sodium chloride were dissolved in one liter of distilled water; and the resulting solution was adjusted to pH 7, using sodium hydroxide, and was sterilized under heating, to prepare the medium.

(B) LB Medium (pH 2):
10 g of trypton, 5 g of yeast extract, and 10 g of sodium chloride were dissolved in one liter of distilled water; and the resulting solution was adjusted to pH 2, using sulfuric acid, and was then sterilized under heating, to prepare the medium.

(C) LB Medium (pH 4.5):
10 g of trypton, 5 g of yeast extract, and 10 g of sodium chloride were dissolved in one liter to distilled water; and the resulting solution was adjusted to pH 4.5, using sulfuric acid, and was then sterilized under heating, to prepare the medium.

(D) LB Medium (pH 9.5):
10 g of trypton, 5 g of yeast extract, and 10 g of sodium chloride were dissolved in one liter of distilled water; and the resulting solution was adjusted to pH 9.5, using sodium hydroxide, and was then sterilized under heating, to prepare the medium.

(E) LB Medium (pH 12):
10 g of trypton, 5 g of yeast extracts and 10 g of sodium chloride were dissolved in one liter of distilled water; and the resulting solution was adjusted to pH 12, using sodium hydroxide, and was then sterilized under heating, to prepare the medium.

(F) TSB Medium:
30 g of TSB (trypticase soy broth) was dissolved in one liter of distilled water; and the resulting solution was sterilized under heating, to prepare the medium.

(G) TSB/Sodium Carbonate Medium:
30 g of TSB (tryplicase soy broth) and 5 g of sodium carbonate separately sterilized (0.5% of distilled water) were dissolved in one liter of distilled water; and the resulting solution was sterilized under heating to prepare the medium.

(H) TSB Medium (pH 5.6):
30 g of TSB (trypticase soy broth) was dissolved in one liter of distilled water; and the resulting solution was sterilized under heating, and was then adjusted to pH 5.6 using hydrochloric acid, to prepare the medium.

(I) YPD Medium:
10 g of yeast extract, 20 g of Bactopeptone, and 20 g of glucose were dissolved in one liter of distilled water and sterilized under heating, to prepare the medium.

(J) HORIKOSHI-II Medium:
10 g of soluble starch, 5 g of polypeptone, 5 g of yeast extract, 1 g of dipotassium hydrogen phosphate, and 0.2 g of magnesium sulfate.7$H_2O$ were dissolved in 0.8 mL of distilled water; and the resulting solution was adjusted to pH 7.5, using aqueous sodium hydroxide solution. Separately, 0.2 liter of an aqueous 10% sodium hydrogen carbonate solution was prepared. These were sterilized under heating and mixed together, to prepare the medium.

(K) BA Medium:
1 g of yeast extract, 0.2 g of ammonium sulfate, 0.5 g of magnesium sulfate.7$H_2O$, 0.25 g of calcium chloride 2$H_2O$, and 0.6 g of potassium dihydrogen phosphate were dissolved in 0.5 liter of distilled water; and the resulting solution was adjusted to pH 3, using sulfuric acid. 1 g of glucose was dissolved in 0.5 liter of distilled water. These were sterilized under heating and mixed together, to one liter.

(L) SUFOLOBUS Medium:
1 g of yeast extract, 1.3 g of ammonium sulfate, 0.28 g of potassium dihydrogen phosphate, 0.25 tg of magnesium sulfate.7$H_2O$, 0.07 g of calcium chloride.2$H_2O$, 0.02 g of iron (III) chloride.6$H_2O$, 1.8 mg of manganese chloride.4$H_2O$, 4.5 mg of sodium tetraborate, 0.22 mg of zinc sulfate.7$H_2O$, 0.05 mg of copper (II) chloride.2$H_2O$, 0.03 mg of sodium molybdenate, 0.03 mg of vanadium (IV) sulfate oxide.2$H_2O$, and 0.01 mg of cobalt (II) chloride.6$H_2O$ were dissolved in one liter of distilled water; and the resulting solution was adjusted to pH 2, using sulfuric acid, and sterilized by filtration, to prepare the medium.

(M) Nutrient Medium (pH 7):
8 g of Nutrient broth (manufactured by DIFCO) was dissolved In one liter of distilled water, and sterilized under heating to prepare the medium.

(N) Nutrient Medium (pH 2):
8 g of Nutrient broth (manufactured by DIFCO) was dissolved in one liter of distilled water, sterilized under heating and then adjusted to pH 2, using sulfuric acid, for use.

(O) Nutrient Medium (pH 9.5):
8 g of Nutrient broth (manufactured by DIFCO) was dissolved in one liter of distilled water sterilized under heating and adjusted to pH 9.5, using aqueous 10% sodium carbonate solution and aqueous 1N sodium hydroxide solution separately sterilized, to adjust the total volume to one liter.

(P) Nutrient Medium (pH 12):
8 g of Nutrient broth (manufactured by DIFCO) was dissolved in one liter of distilled water, sterilized under heating and adjusted to pH 12, using aqueous 10% sodium carbonate solution and aqueous 1N sodium hydroxide solution separately sterilized, to adjust the total volume to one liter.

(Q) SCD Medium (pH 7):
15 g of peptone made of casein, 5 g of peptone made of soybean, and 5 g of sodium chloride were dissolved in one liter of distilled water, and sterilized under heating, for use (at pH 6.9, without pH adjustment).

(R) SCD Medium (pH 2):
15 g of peptone made of casein, 5 g of peptone made of soybean, and 5 g of sodium chloride were dissolved in one liter of distilled water, sterilized under heating and adjusted to pH 2 using sulfuric acid, for use.

(S) SCD Medium (pH 4.5):

15 g of peptone made of casein, 5 g of peptone made of soybean, and 5 g of sodium chloride were dissolved in one liter of distilled water, sterilized under heating and adjusted to pH 4.5 using sulfuric acid, for use.

(T) SCD Medium (pH 12)

15 g of peptone made of casein, 5 g of peptone made of soybean, and 5 g of sodium chloride were dissolved in 0.8 liter of distilled water, sterilized under heating and adjusted to pH 12, using aqueous 10% sodium carbonate solution and aqueous 1N sodium hydroxide solution separately sterilized, to adjust the total volume to one liter.

(U) TM Medium:

0.5 mL of sulfuric acid, 2.2 of manganese (II) sulfate.$5H_2O$, 0.5 g of zinc sulfate.$7H_2O$, 0.5 g of boric acid, 0.016 g of copper sulfate, 0.025 g of disodium molybdenate (IV).$2H_2O$ and 0.046 g of cobalt (II) chloride.$6H_2O$ were dissolved in one liter of distilled water, and the resulting mixture was defined as Nitsch's trace elements.

1 g of nitrilotriacetic acid, 0.6 g of calcium sulfate.$2H_2O$, 1 g of magnesium sulfate.$7H_2O$, 0.08 g of sodium chloride, 1.03 g of potassium nitrate, 6.89 g of sodium nitrate, 1.11 g of disodium hydrogen phosphate, 10 mL of aqueous 0.03% iron (III) chloride solution, and 10 mL of Nitsch's trace elements were dissolved in one liter of distilled water, and adjusted to pH 8.2 using aqueous sodium hydroxide solution, to prepare Castenholz basal salt solution.

4 g of polypeptone, 2 g of yeast extract 1 g of sodium chloride, and 10 mL of Castenholz basal salt solution were added to and dissolved in one liter of distilled water, adjusted to pH 7.2 using aqueous sodium hydroxide solution and sterilized under heating.

Example 1

(i) Preparation of Cellulose Gel

Crystalline cellulose (Funacel manufactured by Funakoshi) was added to an aqueous saturated (59%) solution of calcium thiocyanate.$4H_2O$ (manufactured by WAKO PURE CHEMICAL) to a concentration of 3%, for agitation at ambient temperature for one hour, to prepare a cellulose dispersion. After 20 mL of the resulting cellulose dispersion was divided in a glass Petri dish (an outer diameter of 90 mm and a depth of 17 mm), the dish was placed in an autoclave (manufactured by TOMY SEIKO; KS-243) for heating at 120° C. for one minute, to heat and dissolve cellulose. The cellulose solution was left to be cooled at ambient temperature overnight, for solidification. Then, calcium thiocyanate in the solidified cellulose was rinsed in methanol and running water, and continuously rinsed under mild agitation in a water tank containing 5 L of distilled water. While exchanging water at a frequency of twice daily, rinsing was terminated just when the conductivity of the rinse solution reached 5 µS/cm or less, to obtain a cellulose gel.

FIGS. 1 and 2 show scanning electron microscope pictures of the cellulose gel thus obtained. FIG. 1 is a picture at a magnification×10,000 and FIG. 2 is a picture at a magnification×100,000. These indicate that the cellulose gel is a porous structure in a network structure with a cellulose backbone and with large pores.

Absolutely no change in the shape of the cellulose gel such as no softening or melting was observed even after heating and sterilization at 120° C. for 9 hours in the autoclave. It is shown that the cellulose gel has very excellent thermal stability.

For comparison a similar heating test was done on a solid medium using agar as the medium-solidifying component. The solid medium was dissolved by heating and sterilization in an autoclave at 120° C. for 15 minutes. Similarly, a solid medium using gellan gum as the medium-solidifying component was dissolved by heating and sterilization in an autoclave at 120° C. for 15 minutes.

(ii) Preparation of Solid Cellulose Medium

After the cellulose gel obtained above in (i) was heated and sterilized, 20 mL of the LB medium (pH 7) at a 2× concentration was overlaid thereon; after the resulting medium was left to stand under mild agitation for 4 hours, an excess of the medium was removed, to obtain the LB (pH 7) cellulose medium. Instead of the LB medium (pH 7), there were used the LB medium (pH 2), the LB medium (pH 4.5) the LB medium (pH 9.5), the LB medium (pH 12) the Nutrient (pH 7) medium, Nutrient (pH 2) medium, Nutrient (pH 12) medium, SCD (pH 4.5) medium, SCD (pH 7) medium, SCD (pH 2) medium, and SCD (pH 12) medium, to obtain the LB (pH 2) cellulose medium, the LB (pH 4.5) cellulose medium, the LB (pH 9.5) cellulose medium, the LB (pH 12) cellulose medium, the Nutrient (pH 7) cellulose medium, Nutrient (pH 2) cellulose medium, Nutrient (pH 12) cellulose medium, SCD (pH 7) cellulose medium SCD (pH 2) cellulose medium, SCD (pH 4.5) cellulose medium, and SCD (pH 12) cellulose medium.

Petri dishes individually containing the various cellulose media thus obtained were sealed with vinyl tape, and were then left to stand incubators individually kept at 60° C., 70° C. and 80° C. As the standing time passed, the states of the solid cellulose media were visually observed. As shown in the results in Table 1, the solid cellulose media kept the states and shapes stably without softening or dissolution, at any temperatures or pH conditions even after 7 days passed under the conditions. Thus, the media could be used for solid culturing.

Comparative Example 1

In the same manner as in Example 1, above, agar was used instead of the cellulose gel as the medium-solidifying component, to prepare the LB (pH 7) agar medium, the LB (pH 2) agar medium, the LB (pH 4.5) agar medium, the LB (pH 9.5) agar medium, the LB (pH 12) agar medium, the Nutrient (pH 7) agar medium, the Nutrient (pH 2) agar medium, the Nutrient (pH 9.5) agar medium, the Nutrient (pH 12) agar medium, the SCD (pH 7) agar medium, the SCD (pH 2) agar medium, the SCD (pH 4.5) agar medium, and the SCD (pH 12) agar medium. Petri dishes individually containing these agar media were sealed with vinyl tape, and were then left to stand in incubators individually kept at 60° C., 70° C. and 80° C. As the standing time passed, the states of the agar media were visually observed. Consequently, the LB (pH 2) agar medium, the LB (pH 4.5) agar medium, the LB (pH 9.5) agar medium, the LB (pH 12) agar medium, the Nutrient (pH 7) agar medium, the Nutrient (pH 2) agar medium, the Nutrient (pH 9.5) agar medium, the Nutrient (ph 12) agar medium, the SCD (pH 2) agar medium, the SCD (pH 4.5) agar medium, and the SCD (ph 12) agar medium were softened and dissolved at 70° C., while all the media were softened and dissolved at 80° C. Therefore, these media were at states never usable for solid culturing.

Comparative Example 2

In the same manner as in Example 1, (ii) above, gellan gum was used instead of the cellulose gel as the medium-solidifying component, to prepare the LB (pH 7) gellan gum medium, the LB (pH 2) gellan gum medium, the LB (pH 4.5) gellan gum medium, the LB (pH 9.5) gellan gum medium, the LB (pH 12) gellan gum medium, the Nutrient (pH 7) gellan gum medium, the Nutrient (pH 2) gellan gum medium, the Nutrient (pH 12) gellan gum medium, the SCD (pH 7) gellan gum medium, the SCD (pH 2) gellan gum medium, the SCD (pH 4.5) gellan gum medium, and the SCD (pH 12) gellan gum medium. Petri dishes individually containing these gellan gum media were sealed with vinyl tape, and were then left to stand in incubators individually kept at 60° C., 70° C. and 80° C. As the standing time passed, the states of the gellan gum media were visually observed. Consequently, the Nutrient (pH 7) gellan gum medium, the Nutrient (pH 2) gellan gum medium, and the Nutrient (pH 12) gellan gum medium were softened and dissolved at 60° C., while the SCD (pH 2) medium was softened and dissolved at 70° C. and all the media were softened and dissolved at 80° C. Therefore, these media were at states never usable for solid culturing.

Example 2

(iii) Culturing *Escherichia coli* in the Solid Cellulose Medium

In the same manner as in Example 1, the LB (pH 7) cellulose medium was prepared. *Escherichia coli* strain W3110 was preliminarily cultured in the LB medium at 37° C. to $A_{600}$ of 1 to 1.5. The liquid culture was diluted with 0.9% physiological saline to a bacterial concentration of $1\times10^3$ cells/mL. Then, 0.1 mL of the dilution was plated on the LB (pH 7) cellulose medium, using a spreader, for culturing in an incubator kept at 37° C. for 16 to 18 hours. Subsequently, the number of colonies was counted. As a comparative control, culturing was done on the LB (pH 7) agar medium, to compare the number of colonies with that on the LB (pH 7) cellulose medium. Consequently, the number of colonies of *Escherichia coli* was around 100, both on the LB (pH 7) cellulose medium and on the LB (pH 7) agar medium. Thus, *Escherichia coli* grew at the same level on the LB (pH 7) cellulose medium as that on the LB (pH 7) agar medium.

Example 3

(iv) Culturing *Bacillus* on Solid Cellulose Medium

In the same manner as in Example 1 the LB (pH 7) cellulose medium was prepared. *Bacillus subtilis* strain 168 was preliminarily cultured in the LB medium at 37° C. to $A_{600}$ of 1 to 1.5. The liquid culture was diluted with 0.9% physiological saline to a bacterial concentration of $1\times10^3$ cells/mL. Then, 0.1 mL of the dilution was plated on the LB (pH 7) cellulose medium, using a spreader, for culturing in an incubator kept at 37° C. for 16 to 18 hours. Subsequently, the number of colonies was counted. As a comparative control, culturing was done on the LB (pH 7) agar medium, to com-

TABLE 1

Stability comparison of agar media, gellan gum media and cellulose media

| Medium-solidifying component/medium | | 60° C. pH | | | 70° C. pH | | | | | 80° C. pH | | |
|---|---|---|---|---|---|---|---|---|---|---|---|---|
| | | 2 | 7 | 12 | 2 | 4.5 | 7 | 9.5 | 12 | 2 | 7 | 12 |
| Cellulose | LB | ○ (7 days) | ○ (7 days) | ○ (7 days) | ○ (7 days) | ○ (7 days) | ○ (7 days) | ○ (7 days) | ○ (7 days) | ○ (7 days) | ○ (7 days) | ○ (7 days) |
| | Nutrient | ○ (7 days) | ○ (7 days) | ○ (7 days) | ○ (7 days) | | ○ (7 days) | | ○ (7 days) | ○ (7 days) | ○ (7 days) | ○ (7 days) |
| | SCD | ○ (7 days) | ○ (7 days) | ○ (7 days) | ○ (7 days) | ○ (7 days) | ○ (7 days) | | ○ (8 days) | ○ (7 days) | ○ (7 days) | ○ (7 days) |
| Agar | LB | ○ (7 days) | ○ (7 days) | ○ (7 days) | X (8 hours) | X (7 days) | ○ (7 days) | X (7 days) | X (7 days) | X (15 hours) | X (15 hours) | X (15 hours) |
| | Nutrient | ○ (7 days) | ○ (7 days) | ○ (7 days) | X (1 day) | | X (1 day) | X (2 days) | X (1 day) | X (1 day) | X (1 day) | X (1 day) |
| | SCD | ○ (7 days) | ○ (7 days) | ○ (7 days) | X (1 day) | X (9 days) | ○ (9 days) | | X (3 days) | X (1 day) | X (5 hours) | X (1 day) |
| Gellan gum | LB | ○ (7 days) | ○ (7 days) | ○ (7 days) | ○ (7 days) | ○ (7 days) | ○ (7 days) | ○ (7 days) | ○ (7 days) | X (2 days) | X (2 days) | X (2 days) |
| | Nutrient | X not solidified | X not solidified | X not solidified | X not solidified | | X not solidified | | X not solidified | X not solidified | X not solidified | X not solidified |
| | SCD | ○ (7 days) | ○ (7 days) | ○ (7 days) | X (5 days) | ○ (9 days) | ○ (9 days) | | ○ (9 days) | X (1 day) | X (2 days) | X (19 hours) |

○: usable.
X: not usable.
The numerical figures in the parenthesis below the symbols show the standing times (in hours or days).

pare the number of colonies with that on the LB (pH 7) cellulose medium. Consequently, the number of colonies of *Bacillus subtilis* was about 120 to 150, both on the LB (pH 7) cellulose medium and on the LB (pH 7) agar medium. Thus, the *Bacillus subtilis* strain grew at the same level on the LB (pH 7) cellulose medium as that on the LB (pH 7) agar medium.

Example 4

(v) Culturing Yeast Bacterium on Solid Cellulose Medium

Using the YPD medium instead of the LB (pH 7) medium, YPD cellulose medium was prepared in the same manner as in Example 1. *Saccharomyces cerevisiae* YPH499 was preliminarily cultured in the YPD culture broth at 25° C. to $A_{600}$ of 3. The liquid culture was diluted with 0.9% physiological saline to a bacterial concentration of $1 \times 10^3$ cells/mL. Then, 0.1 mL of the dilution was plated on the YPD cellulose medium, using a spreader, for culturing in an incubator kept at 25° C. for 2 days. Subsequently, the number of colonies was counted. As a comparative control, culturing was done on the YPD agar medium, to compare the number of colonies with that on the YPD cellulose medium. Consequently, the number of colonies of yeast was around 140 on the YPD cellulose medium, while the number thereof was around 130 on the YPD agar medium. Thus, the yeast strain grew at the same level on the YPD cellulose medium as that on the YPD agar medium.

Example 5

(vi) Culturing Alkaliphilic Bacterium of the Genus *Bacillus* on Solid Cellulose Medium Using the HORIKOSHI-II medium instead of the LB (pH 7) medium HORIKOSHI-II cellulose medium was prepared in the same manner as in Example 1. Alkaliphilic *Bacillus halodurans* strain C-125 was preliminarily cultured in the HORIKOSHI-II agar medium. A number of colonies was collected and diluted with aqueous 10 mM magnesium sulfate solution to $1 \times 10^3$ cells/mL. Then, 0.1 mL of the dilution was plated on the HORIKOSHI-II cellulose medium, using a spreader, for culturing in an incubator kept at 37° C. for 16 to 18 hours. Subsequently, the number of colonies was counted. As a comparative control, culturing was done on the HORIKOSHI-II agar medium, to compare the number of colonies with that on the HORIKOSHI-II cellulose medium. Consequently, the number of colonies was around 191 on the HORIKOSHI-II cellulose medium, while the number thereof was around 186 on the HORIKOSHI-II agar medium. Thus, *Bacillus halodurans* C-125 grew at the same level on the HORIKOSHI-II cellulose medium as that on the HORIKOSHI-II agar medium.

Additionally a TSB/sodium carbonate cellulose medium was prepared in the same manner as in Example 1, using the TSB/sodium carbonate medium instead of the LB (pH 7) medium. Alkaliphilic *Bacillus agaradhaerans* strain JAMB-602 was preliminarily cultured in the TSB/sodium carbonate medium at 37° C. to $A_{600}$ of 1 to 1.5. The liquid culture was diluted with 0.9% physiological saline to a bacterial concentration of $1 \times 10^3$ cells/mL. Then, 0.1 mL of the dilution was plated on the TSB/sodium carbonate cellulose medium, using a spreader, for culturing in an incubator kept at 37° C. for 16 to 18 hours. Subsequently, the number of colonies was counted. As a comparative control, culturing was done on the TSB/sodium carbonate agar medium, to compare the number of colonies with that on the TSB/sodium carbonate cellulose medium. Consequently, *Bacillus agaradhaerans* JAMB-602 grew at the same level on the TSB/sodium carbonate cellulose medium as that on the TSB/sodium carbonate agar medium and formed colonies of about 200 on the TSB/sodium carbonate cellulose medium.

Example 6

(vii) Culturing Basidiomycetes on Solid Cellulose Medium

A TSB (pH 5.6) cellulose medium was prepared in the same manner as in Example 1, using the TSB (pH 5.6) medium instead of the LB (pH 7) medium. *Irpex lacteus* strain NBRC5367 preliminarily cultured in the agar medium was plated on the center of a plate, for culturing in at ambient temperature for 8 days. As a comparative control, culturing was done on the TSB (pH 5.6) agar medium to compare the growth with the growth on the TSB (pH 5.6) cellulose medium. *Irpex lacteus* NBRC 5367 grew at the same level on the TSB (pH 5.6) cellulose medium as that on the TSB (pH 5.6) agar medium.

On the TSB (pH 5.6) cellulose medium, additionally, cellulose was decomposed with cellulose generated by *Irpex lacteus* NBRC5367, to form a halo. It was shown that the cellulose medium was applicable to the screening for cellulose-generating bacteria.

Example 7

(viii) Culturing Thermophilic, Acidophilic Bacterium on Solid Cellulose Medium

In the same manner as in Example 1, the BA cellulose medium was prepared, using the BA medium instead of the LB (pH 7) medium. Thermophilic, acidophilic *Alicyclobacillus acidocaldarius* JCM5260 was preliminarily cultured in the BA medium at 70° C. to $A_{600}$ of 0.5. 0.1 mL of the liquid culture was plated on the BA cellulose medium, using a spreader, for culturing at 70° C. for 18 to 24 hours. As a comparative control, culturing was done on the BA agar medium and the BA gellan gum medium, to compare the growth thereon with that on the BA cellulose medium. *Alicyclobacillus acidocaldarius* JCM5260 formed colonies on the BA cellulose medium and on the BA gellan gum medium, while no colony formation was observed on the BA agar medium.

In the same manner as in Example 1, a SULFOLOBUS cellulose medium was prepared, using the SULFOLOBUS medium instead of the LB (pH 7) medium. Thermophilic, acidophilic *Sulfolobus acidocaldarius* DSM639 was preliminarily cultured in the SULFOLOBUS medium at 70° C. to $A_{600}$ of 0.8. The liquid culture was diluted with the SULFOLOBUS medium, to $10^3$ fold. 0.1 mL of the dilution was plated on the SULFOLOBUS cellulose medium, using a spreader, for culturing at 70° C. for 4 days. As a comparative control culturing was done on the SULFOLOBUS agar medium and the SULFOLOBUS gellan gum medium, to compare the growth thereon with that on the SULFOLOBUS cellulose medium. *Sulfolobus acidocaldarius* DSM639 formed colonies on the SULFOLOBUS cellulose medium and on the SULFOLOBUS gellan gum medium, while no colony formation was observed on the SULFOLOBUS agar medium. Culturing was done at 80° C. for 6 days. *Sulfolobus acidocaldarius* DSM639 formed 5 to 6 colonies on the SUL- FOLOBUS cellulose medium and formed one colony on the SULFOLOBUS gellan gum medium. Thus, the bacterium grew better on the SULFOLOBUS cellulose medium.

Example 8

(ix) Culturing Thermophilic Bacterium on Solid Cellulose Medium

In the same manner as in Example 1, the TM cellulose medium was prepared, using the TM medium instead of the LB (pH 7) medium. A thermophilic bacterium *Thermus thermophilus* HB8 was preliminarily cultured in the TM medium at 70° C. to $A_{600}$ of 1 to 1.5. The liquid culture was diluted with aqueous 0.9% sodium chloride solution, to $10^5$ fold. Then, 0.1 mL of the dilution was plated on the TM cellulose medium using a spreader, for culturing in an incubator kept at 70° C. for 17 hours. As a comparative control, culturing was done on the TM agar medium, to compare the growth thereon with that on the TM cellulose medium. The TM gellan gum medium was not solidified at ambient temperature. The bacterium formed colonies on the TM cellulose medium and on the TM agar medium. Because the surface of the TM agar medium was softened, however, the colony shapes were variable. The colonies on the TM cellulose medium were in a uniform shape. Culturing was done at 80° C. for 24 hours. The bacterium formed colonies on the TM cellulose medium. However, the TM agar medium was completely dissolved.

INDUSTRIAL APPLICABILITY

The solid medium using the cellulose gel of the invention can retain the properties and shape in a stable manner without softening or dissolution, at high temperature in a wider pH range or at various salt concentrations, where agar medium as a typical related-art solid medium can hardly retain the properties and shape. Therefore, various microorganisms can now be cultured on solids. Thus, the solid medium can be used for isolating and generating novel microorganisms generating useful enzymes or chemical substances.

The invention claimed is:

1. A solid medium suitable for culturing microorganisms, the solid medium comprising a cellulose gel as a medium-solidifying component, which is a porous gel-like material obtained by dissolving cellulose dispersed in aqueous thiocyanate salt solution by heating, subsequently cooling and solidifying the resulting solution from which solvent is removed, and then permeating a nutrient component suitable for supporting a culture of a microorganism into the resulting cellulose.

2. A solid medium according to claim 1, where the crystallization degree of the cellulose gel is 5 to 70%.

3. A solid medium according to claim 1, where the molecular weight of the cellulose is 10,000 to 2,000,000.

4. A solid medium according to claim 1, where the cellulose gel is a porous cellulose gel structure with a cellulose backbone and at a cellulose concentration of 0.01% or more.

5. A solid medium according to claim 1, where the cellulose gel is a porous gel-like structure at a porosity of 50% or more.

6. The solid medium according to claim 1, which is in a disc form or a column form.

7. A petri dish, comprising the solid medium according to claim 1.

8. A test tube, comprising the solid medium according to claim 1.

* * * * *